(12) United States Patent
Umekawa et al.

(10) Patent No.: US 7,682,442 B2
(45) Date of Patent: Mar. 23, 2010

(54) MEDICAL ADSORBENT AND PROCESS FOR PRODUCTION OF THE SAME

(75) Inventors: Tomomichi Umekawa, Osaka (JP); Tsutomu Kohsaka, Nagoya (JP); Keita Hibi, Gifu (JP); Tomomi Inagaki, Gifu (JP); Toh-ichiro Hatori, Gunma (JP)

(73) Assignees: Futamura Kagaku Kabushiki Kaisha, Aichi-ken (JP); Gun-Ei Kagaku Kogyo Kabushiki Kaisha, Gunma (JP)

( * ) Notice: Subject to any disclaimer, the term of this patent is extended or adjusted under 35 U.S.C. 154(b) by 1619 days.

(21) Appl. No.: 10/751,935

(22) Filed: Jan. 7, 2004

(65) Prior Publication Data

US 2004/0141963 A1 Jul. 22, 2004

(30) Foreign Application Priority Data

Jan. 22, 2003 (JP) .............................. 2003-013668
Dec. 10, 2003 (JP) .............................. 2003-411829

(51) Int. Cl.
C09C 1/44 (2006.01)
A01N 59/00 (2006.01)
A61K 33/44 (2006.01)
C01B 31/02 (2006.01)
C09C 1/48 (2006.01)
C01D 3/00 (2006.01)
A61M 1/16 (2006.01)
B01D 35/00 (2006.01)

(52) U.S. Cl. .................. 106/472; 424/125; 423/450; 423/445 R; 423/449.1; 210/233; 210/437; 428/402

(58) Field of Classification Search ................ 424/125; 252/29.6; 423/450, 445 R, 449.1; 106/472
See application file for complete search history.

(56) References Cited

U.S. PATENT DOCUMENTS 6,309,446 B1 * 10/2001 Nakanoya et al. ............. 95/102

FOREIGN PATENT DOCUMENTS

| EP | 1 249 241 A1 | 10/2002 |
| GB | 2 053 176 A | 2/1981 |
| JP | 06-135841 A1 | 5/1994 |
| JP | 09110409 * | 4/1997 |
| JP | 11-060664 A1 | 3/1999 |
| JP | 2001-114852 A1 | 4/2001 |
| JP | 2002-308785 A1 | 10/2002 |

OTHER PUBLICATIONS

European Search Report for application No. EP 04 00 1189 completed on Apr. 23, 2004.
Yang, Jun-Bing et al., "Preparation and properties of phenolic resin-based activated carbon spheres with controlled pore size distribution", Carbon, vol. 40, No. 6, 2002, pp. 911-916.
EPO Communication of a notice of opposition, App. No. 04001189.2-2123/1440692, Ref. EP 40609, Sep. 22, 2006 (1 page) and Translation of the Opposition by Blücher GmbH dated Sep. 11, 2006 (30 pages).

* cited by examiner

Primary Examiner—Jerry Lorengo
Assistant Examiner—Pegah Parvini
(74) Attorney, Agent, or Firm—Cheng Law Group, PLLC

(57) ABSTRACT

A medical adsorbent which produces minimal side-effects such as constipation, has excellent adsorption for ionic organic compounds such as causative substances of uremia, exhibits adequate adsorption performance at low doses and avoids adsorption of high-molecular compounds necessary for the body, such as enzymes and polysaccharides. The medical adsorbent comprises activated carbon obtained by carbonizing a spherical phenol resin in a nitrogen atmosphere at a temperature of 400-1000° C., activating the carbonized spherical phenol resin at a temperature of 800-1000° C., washing it with dilute hydrochloric acid, heat treating it at a temperature of 150-1000° C. in a mixed gas comprising oxygen and nitrogen and then sorting it; the activated carbon has an area to weight ratio of 500-2000 $m^2/g$, a pore volume of 0.2-1.0 mL/g and a packing density of 0.5-0.75 g/mL.

6 Claims, No Drawings

MEDICAL ADSORBENT AND PROCESS FOR PRODUCTION OF THE SAME

BACKGROUND OF THE INVENTION

1. Field of the Invention

The present invention relates to a medical adsorbent for oral administration comprising activated carbon obtained using a spherical phenol resin as the starting material.

2. Background Art

Medicinal carbon listed in the Japanese Pharmacopeia has conventionally been used for treatment of acute toxicant or drug poisoning and gastrointestinal disease. Such medicinal carbon is usually activated carbon powder obtained using wood or the like as the main starting material, and a curative effect is exhibited because the medicinal carbon adsorbs harmful substances in the gastrointestinal tract and is excreted out of the body while retaining the harmful substances.

Incidentally, since the aforementioned activated carbon powder used as medicinal carbon is simply pulverized, the shapes of the individual particles are non-uniform and therefore the enteric flow property is poor, such that side-effects such as constipation occur after ingestion. Activated carbon is also unsatisfactory because it is generally highly hydrophobic and unsuited for adsorption of ionic organic compounds such as arginine and putrescine, as typical causative substances of uremia or their precursors.

Among attempts to solve these problems there have been disclosed anti-nephrosis agents comprising activated carbon obtained from materials which are resin compounds in spherical or other shapes formed from wood or petroleum- or coal-based pitches and the like as starting materials (for example, Patent Document 1). This activated carbon is prepared using petroleum-based hydrocarbons (pitch) as the starting material and is adjusted to a relatively uniform particle size and then subjected to carbonization and activation. There has also been disclosed an adsorbent for oral administration wherein it is attempted to render the particle sizes of the activated carbon itself relatively uniform while also adjusting the distribution of the pore volume, etc. in the activated carbon (see Patent Document 2). Such medicinal activated carbon which has been obtained with relatively uniform particle sizes and improved enteric flow properties, and activated carbon with enhanced adsorption properties by adjustment of the pores, is administered to a great number of mild chronic renal insufficiency patients.

Medicinal activated carbon must be able to rapidly and efficiently adsorb causative substances of uremia or their precursors. With existing medicinal activated carbon, however, it has been difficult to reduce the particle sizes while maintaining spherical shapes. Also, adjustment of the pores of conventional medicinal activated carbon has been less than satisfactory while the adsorption performance is not always sufficient, and therefore higher daily doses of administration are required. In particular, because chronic renal insufficiency patients are restricted in their intake of water, it has been a major grievance for patients to swallow their doses with small amounts of water.

In addition, the gastrointestinal organs such as the stomach and small intestines are an environment in which various different substances are mixed including compounds-essential to physiological function such as sugars, proteins, and enzymes secreted by the intestinal walls. Medicinal activated carbon therefore preferably has a selective adsorption function which inhibits adsorption of compounds which are essential to physiological function while adsorbing causative substances of uremia.

[Patent Document 1] Japanese Unexamined Patent Publication HEI No. 6-135841 (page 2)

[Patent Document 2] Japanese Unexamined Patent Publication No. 2002-308785 (pages 2-6)

SUMMARY OF THE INVENTION

The present invention, which has been accomplished in light of the circumstances described above, provides a medical adsorbent which produces minimal side-effects such as constipation, has excellent adsorption for ionic organic compounds such as causative substances of uremia, exhibits adequate adsorption performance at low doses and avoids adsorption of high-molecular compounds necessary for the body such as enzymes and polysaccharides, as well as a process for its production.

DETAILED DESCRIPTION OF THE INVENTION

Specifically, the invention according to claim 1 is a medical adsorbent characterized by comprising spherical activated carbon which is activated carbon obtained by carbonizing and activating a spherical phenol resin and which has an area to weight ratio of 500-2000 $m^2/g$, a pore volume of 0.2-1.0 mL/g and a packing density of 0.5-0.75 g/mL.

The invention according to claim 2 is a medical adsorbent according to claim 1, wherein the spherical activated carbon has an area to weight ratio of 800-2000 $m^2/g$ and a mean pore diameter of 1.7-2.0 nm.

The invention according to claim 3 is a medical adsorbent according to claim 1, wherein the spherical activated carbon has an area to weight ratio of 800-2000 $m^2/g$, and the overall pore volume of pores with a mean pore diameter of no greater than 1.0 nm constitutes at least 55% of the total pore volume.

The invention according to claim 4 is a medical adsorbent according to claim 1, wherein the spherical activated carbon has a surface oxide content of at least 0.35 meq/g.

The invention according to claim 5 is a medical adsorbent according to claim 1, wherein the spherical activated carbon has a maximum particle size of no greater than 425 μm and a mean particle size of no greater than 350 μm.

The invention according to claim 6 is a medical adsorbent according to claim 1, wherein the difference between the proportions of particles of no larger than 103 μm before and after powdering of the spherical activated carbon is no greater than 5%.

The invention according to claim 7 is a medical adsorbent according to claim 1, wherein the spherical activated carbon has an overall pore volume of no greater than 0.04 mL/g of pores with pore diameters of 20-1000 nm.

The invention according to claim 8 is a process for production of a medical adsorbent according to any one of claims 1 to 7, which process comprises:

a step of carbonizing a spherical phenol resin in a nitrogen atmosphere at a temperature of 400-1000° C., a step of activating the carbonized spherical phenol resin at a temperature of 800-1000° C., a step of washing the activated spherical phenol resin with dilute hydrochloric acid, a step of heat treatment at a temperature of 150-1000° C. in a mixed gas comprising oxygen and nitrogen after washing the activated spherical phenol resin with dilute hydrochloric acid, and a step of sorting the spherical phenol resin after the heat treatment.

The invention according to claim 9 is the process for production of a medical adsorbent according to claim 8, wherein the spherical phenol resin is obtained using a phenol as the starting material.

The invention according to claim 10 is the process for production of a medical adsorbent according to claim 8, wherein the spherical phenol resin is obtained using phenols including phenol and at least one methyl group bonded to a phenol nucleus as the starting materials.

The medical adsorbent of the present invention comprises activated carbon obtained by carbonization and activation of a spherical phenol resin, and the activated carbon has its area to weight ratio, pore volume, mean pore diameter, particle size and surface oxide content adjusted to allow selective adsorption of ionic organic compounds while adsorbing fewer macromolecules necessary for the body, such as polysaccharides and enzymes, compared to conventional products.

Specifically, the medical adsorbent of the invention may be obtained using a spherical phenol resin as the starting material, as nearly perfectly spherical activated carbon having particle sizes of from a few micrometers to 2-3 mm and having smaller sizes of the pores formed by activation, in comparison to conventional activated carbon made of petroleum pitch, coconut husks or wood. It is therefore suitable for adsorption of ionic organic compounds with relatively low molecular weight (molecular weight of several tens to several hundred). Activated carbon obtained using a spherical phenol resin as the starting material is also harder than conventional medicinal activated carbon and thus more resistant to powdering.

The medical adsorbent of the invention is activated carbon obtained by carbonization and activation of a spherical phenol resin by the production process described in detail in claim 8. The spherical phenol resin is derived from a phenol substance as specified by the invention described in claim 9, and is obtained by the following publicly known production process. First, a phenol and an aldehyde are subjected to condensation reaction at high temperature and high pressure in a pressure-resistant reactor, in the presence of a condensation catalyst such as an alkylamine compound and an emulsifying dispersant such as a high-molecular surfactant with a glucoside bond. Condensation reaction at high temperature and high pressure means condensation of the phenol and aldehyde in the presence of water at a temperature exceeding 100° C. and under a pressure exceeding atmospheric pressure. The reaction is conducted in a reaction system with an aqueous medium containing at least 30% water, with temperature increase while stirring and for a prescribed time at the high temperature and high pressure. After condensation reaction for the prescribed time period, water is added for washing of the high-molecular surfactant and the reaction system temperature is lowered to below 50° C. The resin is then taken out using a Nutsche or the like and washed and dried to obtain the spherical phenol resin. The obtained spherical phenol resin is nearly perfectly spherical because it is shaped into microspheres of a few micrometers to 2-3 mm during stirring in the aqueous system.

As phenols there may be mentioned one or mixtures of two or more from among publicly known phenol derivatives such as phenol, cresol, bisphenol A, styrenated phenol, alkylphenols (xylenol), phenylphenol, resorcinol, catechol, pyrogallol and the like. Resins obtained using phenols including phenol and at least one methyl group bonded to a phenol nucleus as starting materials as specified in claim 10 are preferred from the standpoint of enhancing the ionic organic compound adsorption performance. An example of a phenol resin with at least one methyl group bonded to the phenol nucleus is 3,5-xylenol. The mixing proportion of phenol and 3,5-xylenol in the examples is 20 parts by weight of 3,5-xylenol to 100 parts by weight of phenol. As aldehydes there may be mentioned one or mixtures of two or more from among formaldehyde, acetaldehyde, benzaldehyde, terephthalaldehyde, hydroxybenzaldehyde and furfural.

Preferred examples of spherical phenol resins to be used for the invention include the spherical phenol resins described in Japanese Unexamined Patent Publication HEI No. 11-60664 and Japanese Unexamined Patent Publication No. 2001-114852. Spherical phenol resins have an aromatic structure and can therefore be highly carbonized and activated to obtain activated carbon with a large surface area. Activated carbons comprising spherical phenol resins have smaller pore diameters and higher packing densities than conventional activated carbon wood, coconut husks, petroleum pitch or the like. They are therefore suitable for adsorption of ionic organic compounds with relatively low molecular weights (molecular weights of from a few tens to a few hundred). Because such spherical phenol resins have low ash content including nitrogen, phosphorus, sodium and magnesium and a higher proportion of carbon per unit of mass compared to conventional wood and the like, it is possible to obtain activated carbon with fewer impurities. It is also preferred to use a spherical phenol resin as the starting material and maintain the spherical form for the activated carbon as specified according to the invention, because the form is tougher, the flow property of the activated carbon in the gastrointestinal tract is improved, and the possibility of causing side-effects such as constipation, as occurs with medicinal carbon of the prior art, is greatly reduced.

The process for production of the medical adsorbent of the invention according to claim 8 will now be described. The process for production of the medical adsorbent of the invention comprises a step of carbonizing the aforementioned spherical phenol resin, activating it, washing it with dilute hydrochloric acid, heat treating it, and sorting it.

The step of carbonizing the spherical phenol resin will be explained first. Carbonization of the spherical phenol resin is carried out by placing the spherical phenol resin in a firing furnace such as a stationary electric furnace, and heating it in a nitrogen atmosphere. Here "nitrogen atmosphere" means that the system interior is exchanged with nitrogen gas. The heating temperature is from 400-1000° C. and preferably from 450-700° C.

The carbonized spherical phenol resin is then placed in a heating furnace such as a rotary external heating furnace for activation. The activation method used in the accompanying examples is a gas activation method using water vapor, carbon dioxide or the like, but there is no restriction to this method. The heating temperature is 800-1000° C.

The activated spherical phenol resin is washed with dilute hydrochloric acid. This is followed by adequate rinsing with water so that the pH of the activated carbon after washing with dilute hydrochloric acid is between 5 and 7 as measured according to the method of JIS K1474.

After the washing with dilute hydrochloric acid, the spherical phenol resin is heated in a mixed gas comprising oxygen and nitrogen to increase the surface oxide content of the activated carbon. The oxygen concentration for the heat treatment is 0.1-21 vol %, and the heating temperature is 150-1000° C. and preferably 400-800° C.

The heat treated activated carbon is then sorted using a sieve screen to adjust and separate the particle sizes of the activated carbon of the spherical phenol resin, to obtain the activated carbon as a medical adsorbent according to the invention. The sorting removes the activated carbon with large particle sizes that has a slow adsorption rate and cannot adequately exhibit its adsorption power. Activated carbon according to the invention as described in claims 1 to 7 obtained by this process will now be explained.

As specified in claim 1, the spherical activated carbon obtained by the aforementioned production process has an area to weight ratio of 500-2000 $m^2/g$, a pore volume of 0.2-1.0 mL/g and a packing density of 0.5-0.75 g/mL. As will be appreciated by the adsorption performance exhibited for arginine, putrescine, pullulan and trypsin indicated in Examples 1-4 below, the activated carbon preferably has the properties specified above for the purpose of adsorbing ionic organic compounds which are causative substances of uremia, and avoiding adsorption of high-molecular compounds needed by the body, such as enzymes and polysaccharides. If the activated carbon has an area to weight ratio of less than 500 $m^2/g$ or a packing density of greater than 0.75 g/mL, the pore volume of the activity carbon will be reduced, possibly leading to a reduced volume of ionic organic compounds that can be adsorbed. On the other hand, if it has an area to weight ratio of greater than 2000 $m^2/g$ or a packing density of less than 0.5 g/mL, the pore diameters of the activated carbon will be too large, possibly leading to adsorption of high-molecular compounds including proteins (enzymes) such as trypsin and polysaccharides such as pullulan. This can also undesirably lower the packing density of the activated carbon and require large volumes of ingestion. Also, if the pore volume of the activated carbon is less than 0.2 mL/g, the reduced pore volume will result in insufficient adsorption power for ionic organic compounds, while if the pore volume is greater than 1.0 mL/g, the excessive pore volume will lower the activated carbon strength and make it difficult to maintain spherical shapes, possibly causing side-effects such as constipation due to powdering during or after ingestion.

As specified in claim 2, the spherical activated carbon has an area to weight ratio of 800-2000 $m^2/g$ and a mean pore diameter of 1.7-2.0 nm. By adjusting the mean pore diameter of the activated carbon to within this range, it is possible to obtain activated carbon which exhibits excellent adsorption for relatively low molecular ionic organic compounds with low molecular weights of from a few tens to a few hundred, but which at the same time does not adsorb high-molecular compounds necessary for the body such as enzymes and polysaccharides with molecular weights of from a few thousand to a few tens of thousands. The mean pore diameter of the activated carbon is preferably not greater than 2.0 nm because numerous pores will be present that adsorb macromolecules necessary for the body such as enzymes and polysaccharides. Also, if the mean pore diameter of the activated carbon is less than 1.7 nm, the pore volume itself will be smaller and the adsorption power may consequently be reduced.

As specified in claim 3, the spherical activated carbon has an area to weight ratio of 800-2000 $m^2/g$ and the overall pore volume of pores with a mean pore diameter of no greater than 1.0 nm constitutes at least 55% of the total pore volume. Since the molecular weights of ionic organic compounds such as uremia toxins including urea, guanidine and the like are from several tens to several hundred (MW), the pore diameters which contribute to adsorption of such ionic organic compounds are thought to be up to 1.0 nm in size. Consequently, if the overall pore volume of pores with a mean pore diameter of no-greater than 1.0 nm constitutes less than 55% of the total pore volume, the proportion of pores with large pore diameters will be greater, not only increasing the number of pores which do not contribute to adsorption of ionic organic compounds, but also resulting in adsorption of macromolecules necessary for the body, such as enzymes and polysaccharides.

As specified in claim 4, the spherical activated carbon preferably has a surface oxide content of at least 0.35 meq/g. By heat treating the activated carbon in the manner described below to enhance the surface oxide content, i.e. to increase the functional groups on the activated carbon surface, it is possible to improve the adsorption performance for ionic organic compounds. The surface oxides of activated carbon are hydrophilic functional groups such as carboxyl and hydroxyl groups, for the most part. A surface oxide content of below 0.35 meq/g will therefore lower the hydrophilicity of the activated carbon and reduce the adsorption power for hydrophilic ionic organic compounds.

As specified in claim 5, the spherical activated carbon preferably has a maximum particle size of no greater than 425 µm and a mean particle size of no greater than 350 µm, from the standpoint of increasing the catalyst efficiency for ionic organic compounds to be adsorbed for enhanced adsorption performance, as will be readily apparent from the examples below. If the maximum particle size is greater than 425 µm or the mean particle size is greater than 350 µm, the catalyst efficiency for ionic organic compounds to be adsorbed is reduced, thereby lowering the adsorption rate to a degree which may result in insufficient adsorption performance for ionic organic compounds.

As specified in claim 6, the difference between the proportions of particles of no larger than 103 µm before and after powdering of the spherical activated carbon is preferably no greater than 5%. If the difference between the particle proportions is greater, it may not be possible to retain the spherical shapes as a result of powdering during enteric flow after ingestion.

As specified in claim 7, the overall pore volume of pores with pore diameters of 20-1000 nm is preferably no greater than 0.04 mL/g. Pores with pore diameters of 20-1000 nm are not only unsuited for adsorption of target ionic organic compounds with molecular weights of several tens to several hundred, such as uremia toxins, but also potentially adsorb high-molecular compounds such as enzymes and polysaccharides. It is therefore not preferred for the overall pore volume of pores with pore diameters of 20-1000 nm to be greater than 0.04 mL/g, because this will not only increase the number of pores which do not contribute to adsorption of ionic organic compounds but will also result in more adsorption of high-molecular compounds necessary for the body, such as proteins (enzymes).

EXAMPLES

Activated carbons for Examples 1-11 according to the invention and activated carbons for Comparative Examples 1-6 were prepared, and the area to weight ratio ($m^2/g$), pore volume (mL/g), mean pore diameter (nm), volume of pores with a mean pore diameter of no greater than 1 nm (%), packing density (g/mL), mean particle size (µm), surface oxide content (meq/g) and powdering (%) of each was measured.

Area to weight ratio ($m^2/g$): The nitrogen adsorption isotherm was measured at 77 K using a BELSORP 18PLUS by Nihon Bell Co., Ltd., and the value was determined by the BET method.

Pore volume (mL/g): The Gurvitsch law was applied for a pore diameter range of 0.6-20 nm, and the value was determined from the nitrogen adsorption based on liquid nitrogen at a relative pressure of 0.953, using a BEL- SORP 18PLUS by Nihon Bell Co., Ltd. For the pore diameter range of 20-1000 nm, measurement was performed by mercury porosimetry using an AUTOPORE 9520 by Shimadzu Laboratories.

Mean pore diameter (nm): The value was determined by formula 1 below, with the assumption of cylindrical pore shapes.

Volume of pores with mean pore diameter of $\leq 1$ nm (%): The pore distribution was determined, and the proportion of the overall pore volume of pores with pore diameters of no greater than 1.0 nm with respect to the total pore volume was calculated. The pore distribution was determined using a BELSORP 18PLUS by Nihon Bell Co., Ltd., with the pore diameter range of 2 nm and greater analyzed by the D-H method (Dollimore-Heal method) based on the aforementioned nitrogen adsorption isotherm and the pore diameter range of smaller than 2 nm analyzed by the MP (micropore) method according to a t plot based on the nitrogen adsorption isotherm.

Packing density (g/mL): The value was determined by the method according to JIS K1474.

Mean particle size (μm): The value was determined by the light scattering method using a SALD3000S by Shimadzu Laboratories.

Surface oxide content (meq/g): The Boehm method was applied, shaking the activated carbon in a 0.05 N aqueous sodium hydroxide solution, filtering it and titrating the filtrate with 0.05 N aqueous hydrochloric acid, with the obtained value used as the basis for measurement.

Powdering (%): The difference in the proportions of particles of no larger than 103 μm before and after powdering of the spherical activated carbon was determined as the degree of powdering. Specifically, 0.5 g of activated carbon was added to 50 ml of water, the mixture was vigorously stirred with a stirrer for 3 hours, the mean particle size of the activated carbon after stirring was determined by the light scattering method using a SALD3000S by Shimadzu Laboratories, the proportion of particles of no larger than 103 μm was read from the particle size distribution as the proportion of particles (%) of no larger than 103 μm after powdering, and the powdering (%) was determined by formula 2 below.

$$\text{Mean particle diameter (nm)} = \left[\frac{\text{pore volume (mL/g)}}{\text{area/weight ratio (m}^2\text{/g)}}\right] \times 4 \times 1000 \quad \text{(formula 1)}$$

$$\text{Powdering (\%)} = \begin{bmatrix} \text{proportion (\%) of particles} \\ \text{no larger than 103 } \mu\text{m} \\ \text{after powdering} \end{bmatrix} - \begin{bmatrix} \text{proportion (\%) of particles} \\ \text{no larger than 103 } \mu\text{m} \\ \text{before powdering} \end{bmatrix} \quad \text{(formula 2)}$$

The activated carbon for Examples 1-11 according to the invention and the activated carbon for Comparative Examples 1-6 were examined in regard to adsorption performance for ionic organic compounds and for polysaccharides and enzymes, by an adsorption performance test conducted by the method described below. Arginine and putrescine were used as the adsorbed substances for the ionic organic compound adsorption performance test, pullulan was used as the adsorbed substance for the polysaccharide adsorption performance test, and trypsin was used as the adsorbed substance for the enzyme adsorption performance text.

The ionic organic compound adsorption performance was determined by the following method using arginine and putrescine as ionic organic compounds. First, the arginine adsorption performance was determined by reacting the activated carbon of the examples and comparative examples with an arginine solution and calculating the mass of adsorbed arginine from the concentration of TOC (Total Organic Carbon) in the solution. Specifically, arginine used as the adsorbed substance was dissolved in phosphate buffer at pH 7.4 to prepare an arginine standard solution with an arginine concentration of 0.1 g/L, and then 0.5 g and 0.25 g of the activated carbon of each of the examples and comparative examples were added to 50 mL of the arginine standard solution for contact shaking for 3 hours at a temperature of 37° C., after which each reaction mixture was filtered, the TOC concentration (mg/L) of each filtrate was measured using a total organic carbon analyzer ("TOC5000A" by Shimadzu Laboratories) and the arginine mass of each filtrate was calculated. The arginine adsorption of each filtrate was then calculated by subtracting the arginine mass of the filtrate from the arginine mass of the arginine standard solution, and each arginine adsorption value was divided by the activated carbon-mass (0.5 g or 0.25 g) to obtain the arginine adsorption by weight. The arginine adsorption by volume was obtained by multiplying the arginine adsorption by weight by the packing density.

The putrescine adsorption performance was determined by reacting the activated carbon of the examples and comparative examples with a putrescine solution and calculating the mass of adsorbed putrescine from the concentration of TOC (Total Organic Carbon) in the solution. Specifically, putrescine used as the adsorbed substance was dissolved in phosphate buffer at pH 7.4 to prepare a putrescine standard solution with a putrescine concentration of 0.1 g/L, and this was treated in the same manner as the arginine adsorption performance test described above except that the putrescine standard solution was used instead of the arginine standard solution, after which the putrescine adsorption by weight and the putrescine adsorption by volume were determined.

The polysaccharide adsorption performance was determined by reacting the activated carbon of the examples and comparative examples with a solution of pullulan (molecular weight: approximately 11,800) as the polysaccharide and calculating the mass of adsorbed pullulan from the concentration of TOC (Total Organic Carbon) in the solution. Specifically, pullulan used as the adsorbed substance was dissolved in distilled water to prepare a pullulan standard solution with a pullulan concentration of 0.1 g/L, and this was treated in the same manner as the arginine adsorption performance test described above except that the pullulan standard solution was used instead of the arginine standard solution, after which the pullulan adsorption by weight and the pullulan adsorption by volume were determined.

The enzyme adsorption performance was determined by reacting the activated carbon of the examples and comparative examples with a solution of trypsin as an example of an enzyme, and calculating the mass of adsorbed trypsin from the concentration of TOC (Total Organic Carbon) in the solution. Specifically, trypsin used as the adsorbed substance was dissolved in distilled water to prepare a trypsin standard solution with a trypsin concentration of 0.1 g/L, and then 0.25 g and 0.125 g of the activated carbon of each of the examples and comparative examples were added to 50 mL of the trypsin standard solution for contact shaking for 3 hours at a temperature of 21° C., after which each reaction mixture was filtered, the TOC concentration (mg/L) of each filtrate was measured using a total organic carbon analyzer and the trypsin mass of each filtrate was calculated. The trypsin adsorption was then calculated by subtracting the trypsin mass of the filtrate from the trypsin mass of the trypsin standard solution, and each trypsin adsorption value was divided by the activated carbon mass (0.25 g or 0.125 g) to obtain the trypsin adsorption by weight. The trypsin adsorption by volume was obtained by multiplying the trypsin adsorption by weight by the packing density.

Example 1

An 800 g portion of a spherical phenol resin ("MARIRIN HF-MDC" by Gun Ei Kagaku Kogyo K.K.) was placed in a metal retort vessel (interior volume: 1.5 L) and carbonized by heating for 4 hours at a temperature of 600° C. in a nitrogen atmosphere using a stationary electric furnace. The carbonized spherical phenol resin was activated by heating for 1 hour at 950° C. in water vapor using a rotary external heating furnace, and then washed with a 0.1% aqueous hydrochloric acid solution. The activated carbon was then rinsed with water to a pH of 5-7 as measured according to the method of JIS K1474. The water-washed activated carbon was subjected to heat treatment in a rotary external heating furnace for 3 hours at a temperature of 600° C. in an oxygen-nitrogen mixed gas adjusted to an oxygen concentration of 3 vol %. Finally, it was sorted using a 119-200 mesh (75-125 μm) sieve according to JIS Z8801 to obtain activated carbon for Example 1.

Example 2

Activated carbon for Example 2 was obtained by the same treatment as in Example 1, except that the activation time in water vapor in Example 1 was changed to 1.5 hours.

Example 3

Activated carbon for Example 3 was obtained by the same treatment as in Example 1, except that the activation time in water vapor in Example 1 was changed to 2 hours.

Example 4

Activated carbon for Example 4 was obtained by the same treatment as in Example 1, except that the activation time in water vapor in Example 1 was changed to 3 hours.

Comparative Example 1

Activated carbon for Comparative Example 1 was obtained by the same treatment as in Example 1, except that the activation in water vapor in Example 1 was not carried out for comparison.

Comparative Example 2

Activated carbon for Comparative Example 2 was obtained by the same treatment as in Example 1, except that the activation time in water vapor in Example 1 was changed to 5 hours.

The activated carbon of each of Examples 1-4 and Comparative Examples 1 and 2 was examined in regard to physicochemical properties such as area to weight ratio ($m^2/g$), etc. and adsorption performance for arginine, putrescine, pullulan and trypsin, by the measuring methods explained above. The results are shown in the following Tables 1 and 2.

TABLE 1

|  | Example 1 | Example 2 | Example 3 | Example 4 | Comp. Ex. 1 | Comp. Ex. 2 |
| --- | --- | --- | --- | --- | --- | --- |
| Activation time (hr) | 1 | 1.5 | 2 | 3 | 0 | 5 |
| Sieve mesh (μm) | 125-75 | 125-75 | 125-75 | 125-75 | 125-75 | 125-75 |
| Area/weight ratio ($m^2/g$) | 1115 | 1380 | 1470 | 1630 | 610 | 2190 |
| Pore volume 0.6-20 nm (mL/g) | 0.47 | 0.59 | 0.66 | 0.75 | 0.26 | 1.13 |
| 20-1000 nm | 0.009 | 0.020 | 0.026 | 0.036 | — | 0.098 |
| Mean pore diameter (nm) | 1.69 | 1.71 | 1.80 | 1.83 | 1.69 | 2.06 |
| Volume of pores of pore diameter ≦1 nm (%) | 82.1 | 71.5 | 60.2 | 56.0 | 82.9 | 27.5 |
| Packing density (g/mL) | 0.69 | 0.61 | 0.59 | 0.54 | 0.80 | 0.42 |
| Mean particle size (μm) | 106 | 113 | 117 | 99 | 90 | 84 |
| Surface oxide content (meq/g) | 0.61 | 0.59 | 0.68 | 0.64 | 0.40 | 0.56 |

TABLE 2

|  | Activated carbon addition (g) | Example 1 | Example 2 | Example 3 | Example 4 | Comp. Ex. 1 | Comp. Ex. 2 |
| --- | --- | --- | --- | --- | --- | --- | --- |
| Arginine adsorption by weight (mg/g) | 0.5 | 6.9 | 8.3 | 8.5 | 8.2 | 4.2 | 8.3 |
|  | 0.25 | 10.1 | 13.2 | 13.1 | 12.4 | 4.8 | 12.5 |
| Putrescine adsorption by weight (mg/g) | 0.5 | 2.3 | 4.5 | 4.8 | 4.3 | 1.9 | 4.3 |
|  | 0.25 | 2.4 | 5.8 | 6.2 | 5.3 | 2.0 | 5.2 |
| Pullulan adsorption by weight (mg/g) | 0.5 | 1.0 | 1.2 | 1.3 | 2.9 | 0.1 | 7.2 |
|  | 0.25 | 1.6 | 1.6 | 1.9 | 3.8 | 0.2 | 7.8 |
| Trypsin adsorption by weight (mg/g) | 0.25 | 2.5 | 2.1 | 3.4 | 4.8 | 1.4 | 8.2 |
|  | 0.125 | 3.8 | 3.0 | 4.8 | 6.6 | 2.8 | 10.6 |

TABLE 2-continued

| | Activated carbon addition (g) | Example 1 | Example 2 | Example 3 | Example 4 | Comp. Ex. 1 | Comp. Ex. 2 |
|---|---|---|---|---|---|---|---|
| Arginine adsorption by volume (mg/mL) | 0.5 | 4.7 | 5.0 | 5.0 | 4.4 | 4.9 | 3.5 |
| | 0.25 | 6.9 | 8.1 | 7.8 | 6.7 | 6.9 | 5.2 |
| Putrescine adsorption by volume (mg/mL) | 0.5 | 1.5 | 2.7 | 2.8 | 2.3 | 1.5 | 1.8 |
| | 0.25 | 1.6 | 3.6 | 3.7 | 2.8 | 1.6 | 2.2 |
| Pullulan adsorption by volume (mg/mL) | 0.5 | 0.7 | 0.7 | 0.8 | 1.5 | 0.1 | 3.0 |
| | 0.25 | 1.1 | 1.0 | 1.1 | 2.1 | 0.1 | 3.3 |
| Trypsin adsorption by volume (mg/mL) | 0.25 | 1.8 | 1.3 | 2.0 | 2.6 | 1.1 | 3.4 |
| | 0.125 | 2.7 | 1.9 | 2.9 | 3.5 | 2.2 | 4.4 |

As clearly seen in Table 1 and Table 2, Examples 1 to 4 were confirmed to exhibit adequate adsorption performance in terms of both arginine and putrescine adsorption performance by weight and arginine and putrescine adsorption performance by volume. Particularly apparent is that lengthening of the activation time for increased area to weight ratio and pore volume resulted in a commensurate improvement in adsorption performance. Moreover, the amounts of pullulan and trypsin adsorption (both adsorption by weight and adsorption by volume) are clearly lower than those in Comparative Example 2. In Comparative Example 1, the arginine and putrescine adsorption performances by weight were reduced compared to the examples. It is believed that the lack of water vapor activation resulted in inadequate development of pores in the activated carbon surface. The arginine and putrescine adsorption performances by volume were also reduced in Comparative Example 2 compared to the examples, and this is attributed to the lower packing density of the activated carbon as a result of the increased area to weight ratio. In addition, Comparative Example 2 had greater pullulan and trypsin adsorptions (both adsorption by weight and adsorption by volume) compared to Examples 1 to 4, presumably because a larger area to weight ratio and pore volume means a larger mean pore size, and the decrease in pores with pore diameters of smaller than 1.0 nm and increase in pores with pore diameters of 1.0 nm or greater tends to promote adsorption of polysaccharides or enzymes of large molecular weight.

Next, in order to examine the relationship between the activated carbon particle size and adsorption performance, activated carbon samples for Examples 5 to 8 were prepared with varying mean particle sizes (μm) obtained by varying the mesh of the sieve used.

Example 5

Activated carbon for Example 5 was obtained by the same treatment as in Example 3, except that an 18-36 mesh (850-425 μm) sieve was used instead of the sieve used for sorting in Example 3.

Example 6

Activated carbon for Example 6 was obtained by the same treatment as in Example 3, except that a 36-70 mesh (425-212 μm) sieve was used instead of the sieve used for sorting in Example 3.

Example 7

Activated carbon for Example 7 was obtained by the same treatment as in Example 3, except that a 70-119 mesh (212-125 μm) sieve was used instead of the sieve used for sorting in Example 3.

Example 8

Activated carbon for Example 8 was obtained by the same treatment as in Example 3, except that a 200 mesh (75 μm) sieve was used instead of the sieve used for sorting in Example 3.

Examples 5 to 8 were also examined in regard to physicochemical properties such as area to weight ratio ($m^2/g$), etc. and adsorption performance for arginine, putrescine, pullulan and trypsin, by the measuring methods explained above. The results are shown in the following Tables 3 and 4.

TABLE 3

| | Example 3 | Example 5 | Example 6 | Example 7 | Example 8 |
|---|---|---|---|---|---|
| Activation time (hr) | 2 | 2 | 2 | 2 | 2 |
| Sieve mesh (μm) | 125-75 | 850-425 | 425-212 | 212-125 | ≦75 |
| Area/weight ratio ($m^2/g$) | 1470 | 1390 | 1430 | 1440 | 1385 |
| Pore volume 0.6-20 nm (mL/g) | 0.66 | 0.62 | 0.65 | 0.66 | 0.60 |
| Mean pore diameter (nm) | 1.80 | 1.78 | 1.81 | 1.82 | 1.74 |
| Volume of pores of pore diameter ≦ 1 nm (%) | 60.2 | 61.1 | 64.1 | 58.6 | 61.9 |
| Packing density (g/mL) | 0.59 | 0.61 | 0.61 | 0.60 | 0.61 |
| Mean particle size (μm) | 117 | 458 | 316 | 175 | 60 |
| Surface oxide content (meq/g) | 0.68 | 0.61 | 0.62 | 0.67 | 0.78 |

TABLE 4

|  | Activated carbon addition (g) | Example 3 | Example 5 | Example 6 | Example 7 | Example 8 |
|---|---|---|---|---|---|---|
| Arginine adsorption by weight (mg/g) | 0.5 | 8.5 | 6.6 | 7.8 | 8.1 | 8.7 |
|  | 0.25 | 13.1 | 9.5 | 12.0 | 12.3 | 14.3 |
| Putrescine adsorption by weight (mg/g) | 0.5 | 4.8 | 1.0 | 1.6 | 2.3 | 5.7 |
|  | 0.25 | 6.2 | 1.1 | 1.8 | 2.8 | 7.6 |
| Pullulan adsorption by weight (mg/g) | 0.5 | 1.3 | 0.6 | 0.7 | 0.7 | 1.8 |
|  | 0.25 | 1.9 | 1.0 | 1.2 | 1.1 | 2.4 |
| Trypsin adsorption by weight (mg/g) | 0.25 | 3.4 | 4.5 | 4.3 | 4.8 | 2.2 |
|  | 0.125 | 4.8 | 4.1 | 4.5 | 4.6 | 3.9 |
| Arginine adsorption by volume (mg/mL) | 0.5 | 5.0 | 4.0 | 4.8 | 4.9 | 5.3 |
|  | 0.25 | 7.8 | 5.8 | 7.4 | 7.4 | 8.7 |
| Putrescine adsorption by volume (mg/mL) | 0.5 | 2.8 | 0.6 | 1.0 | 1.4 | 3.5 |
|  | 0.25 | 3.7 | 0.7 | 1.1 | 1.7 | 4.6 |
| Pullulan adsorption by volume (mg/mL) | 0.5 | 0.8 | 0.4 | 0.4 | 0.4 | 1.1 |
|  | 0.25 | 1.1 | 0.6 | 0.8 | 0.7 | 1.5 |
| Trypsin adsorption by volume (mg/mL) | 0.25 | 2.0 | 2.7 | 2.6 | 2.9 | 1.4 |
|  | 0.125 | 2.9 | 2.5 | 2.8 | 2.8 | 2.4 |

As shown by the results for Example 3 and Examples 5 to 8 in Tables 3 and 4, a finer sieve screen and smaller mean particle size (μm) of the obtained activated carbon resulted in enhanced arginine and putrescine adsorption performance.

In order to examine the relationship between the activated carbon surface oxide content and adsorption performance, activated carbon samples for Comparative Examples 3 and 4 and Example 9 were prepared with varying surface oxide contents.

Comparative Example 3

Activated carbon for Comparative Example 3 was obtained by the same treatment as in Example 4, except that the heat treatment in an oxygen-nitrogen mixed gas in Example 4 was not carried out.

Comparative Example 4

Activated carbon for Comparative Example 4 was obtained by the same treatment as in Example 4, except that the heat treatment in an oxygen-nitrogen mixed gas in Example 4 was carried out for 1 hour.

Example 9

Activated carbon for Example 9 was obtained by the same treatment as in Example 4, except that the heat treatment in an oxygen-nitrogen mixed gas in Example 4 was carried out for 2 hours.

Comparative Examples 3 and 4 and Example 9 were examined in regard to surface oxide content (meq/g) and adsorption performance for arginine and putrescine, by the measuring methods explained above. The results are shown in the following Tables 5 and 6.

TABLE 5

|  | Example 4 | Example 9 | Comp. Ex. 3 | Comp. Ex. 4 |
|---|---|---|---|---|
| Heat treatment time (hr) | 3 | 2 | — | 1 |
| Surface oxide content (meq/g) | 0.64 | 0.36 | 0.30 | 0.33 |

TABLE 6

|  | Activated carbon addition (g) | Example 4 | Example 9 | Comp. Ex. 3 | Comp. Ex. 4 |
|---|---|---|---|---|---|
| Arginine adsorption by weight (mg/g) | 0.5 | 8.2 | 8.1 | 7.7 | 7.9 |
|  | 0.25 | 12.4 | 12.6 | 8.9 | 9.7 |
| Putrescine adsorption by weight (mg/g) | 0.5 | 4.3 | 2.3 | 0.1 | 1.3 |
|  | 0.25 | 5.3 | 3.2 | 0.2 | 1.6 |

As clearly seen in Tables 5 and 6, increased surface oxide content achieved by prolonging the heat treatment time in the oxygen-nitrogen mixed gas resulted in enhanced arginine and putrescine adsorption performance.

Next, different types of phenols for spherical phenol resins were used as starting materials for activated carbons, and the difference in performance of the obtained activated carbons was examined.

Example 10

The spherical phenol resin "MARIRIN HF-MDC" used in the aforementioned examples comprises phenol as the only phenol type. For comparison, another spherical phenol resin was obtained under the same conditions as for "MARIRIN HF-MDC", by addition of 20 parts by weight of 3,5-xylenol as an alkylphenol, to 100 parts by weight of phenol. This spherical phenol resin was treated under the same conditions as in Example 3 to obtain activated carbon for Example 10.

Example 11

The same type of phenol as in Example 10 was used to produce activated carbon on an actual production level. A spherical phenol resin of the same type as Example 10 was obtained by addition of 20 parts by weight of 3,5-xylenol to 100 parts by weight of phenol. A 260 kg portion of the spherical phenol resin was placed in a rotary external heating furnace (interior volume: 5 kL) for carbonization by heat treatment for 4 hours at a temperature of 600° C. in a nitrogen atmosphere. The carbonized spherical phenol resin was then activated by heating for 16 hours at a temperature of 850° C. in water vapor, and subsequently washed with 0.1% aqueous hydrochloric acid. The water-washed activated carbon was rinsed with water to a pH of 5-7 as measured according to the method of JIS K1474. The water-washed activated carbon was then subjected to heat treatment in a rotary external heating furnace for 3 hours at a temperature of 600° C. in an oxygen-nitrogen mixed gas adjusted to an oxygen concentration of 3 vol %. Finally, it was sorted using a 119-200 mesh (75-125 μm) sieve according to JIS Z8801 to obtain activated carbon for Example 11.

Examples 10 and 11 were also examined in regard to physicochemical properties such as area to weight ratio ($m^2/g$), etc. and adsorption performance for arginine, putrescine, pullulan and trypsin, by the test methods explained above. The results are shown in the following Tables 7 and 8.

TABLE 7

|  | Example 3 | Example 10 | Example 11 |
|---|---|---|---|
| Activation time (hr) | 2 | 2 | 16 |
| Sieve mesh (μm) | 125-75 | 125-75 | 125-75 |
| Area/weight ratio ($m^2/g$) | 1470 | 1240 | 1350 |
| Pore volume (mL/g) 0.6-20 nm | 0.66 | 0.57 | 0.59 |
| Mean pore diameter (nm) | 1.80 | 1.82 | 1.74 |
| Volume of pores of pore diameter ≦ 1 nm (%) | 60.2 | 70.0 | 71.6 |
| Packing density (g/mL) | 0.59 | 0.64 | 0.66 |
| Mean particle size (μm) | 117 | 105 | 96 |
| Surface oxide content (meq/g) | 0.68 | 0.62 | 1.10 |

TABLE 8

|  | Activated carbon addition (g) | Example 3 | Example 10 | Example 11 |
|---|---|---|---|---|
| Arginine adsorption by weight (mg/g) | 0.5 | 8.5 | 8.9 | 8.8 |
|  | 0.25 | 13.1 | 13.4 | 14.8 |
| Putrescine adsorption by weight (mg/g) | 0.5 | 4.8 | 5.2 | 5.8 |
|  | 0.25 | 6.2 | 6.8 | 7.3 |
| Pullulan adsorption by weight (mg/g) | 0.5 | 1.3 | 2.0 | 1.9 |
|  | 0.25 | 1.9 | 2.9 | 1.0 |
| Trypsin adsorption by weight (mg/g) | 0.25 | 3.4 | 3.3 | 1.4 |
|  | 0.125 | 4.8 | 6.0 | 2.5 |
| Arginine adsorption by volume (mg/mL) | 0.5 | 5.0 | 5.7 | 5.8 |
|  | 0.25 | 7.8 | 8.6 | 9.7 |
| Putrescine adsorption by volume (mg/mL) | 0.5 | 2.8 | 3.3 | 3.8 |
|  | 0.25 | 3.7 | 4.3 | 4.8 |
| Pullulan adsorption by volume (mg/mL) | 0.5 | 0.8 | 1.3 | 1.2 |
|  | 0.25 | 1.1 | 1.8 | 0.7 |
| Trypsin adsorption by volume (mg/mL) | 0.25 | 2.0 | 2.1 | 0.9 |
|  | 0.125 | 2.9 | 3.8 | 1.6 |

As clearly seen in Tables 7 and 8, the activated carbons of Examples 10 and 11 had larger packing densities and enhanced arginine and putrescine adsorption performances (both adsorption by weight and adsorption by volume) compared to the activated carbon of Example 3.

For comparison of the adsorption performances of the present invention products and conventional carbon adsorbents, the chronic renal insufficiency therapeutic agent KUREMESIN ("KUREMESIN granules", by Kureha Chemical Industry Co., Ltd.) was used as Comparative Example 5 and commercially available medicinal carbon listed in the Japanese Pharmacopeia ("Japanese Pharmacopeia Medicinal Carbon" by Kenei Pharmaceutical Co., Ltd.) was used as Comparative Example 6, and the physicochemical properties such as area to weight ratio ($m^2/g$), etc. and adsorption performance for arginine, putrescine, pullulan and trypsin were examined by the measuring methods explained above. The results are shown in the following Tables 9 and 10.

TABLE 9

|  | Example 3 | Comp. Ex. 5 | Comp. Ex. 6 |
|---|---|---|---|
| Activation time (hr) | 2 | — | — |
| Sieve mesh (μm) | 125-75 | — | — |
| Area/weight ratio ($m^2/g$) | 1470 | 1590 | 1254 |
| Pore volume (mL/g) 0.6-20 nm | 0.66 | 0.79 | 0.70 |
| 20-1000 nm | 0.026 | 0.070 | — |
| Mean pore diameter (nm) | 1.80 | 2.00 | 2.22 |
| Volume of pores of pore diameter ≦ 1 nm (%) | 60.2 | 48.3 | 49.2 |
| Packing density (g/mL) | 0.59 | 0.50 | 0.37 |
| Mean particle size (μm) | 117 | 353 | 18 |
| Surface oxide content (meq/g) | 0.68 | 0.47 | 0.30 |

TABLE 10

|  | Activated carbon addition (g) | Example 3 | Comp. Ex. 5 | Comp. Ex. 6 |
|---|---|---|---|---|
| Arginine adsorption by weight (mg/g) | 0.5 | 8.5 | 7.8 | 7.4 |
|  | 0.25 | 13.1 | 11.6 | 10.6 |
| Putrescine adsorption by weight (mg/g) | 0.5 | 4.8 | 2.4 | 1.7 |
|  | 0.25 | 6.2 | 2.9 | 1.8 |
| Pullulan adsorption by weight (mg/g) | 0.5 | 1.3 | 2.3 | 9.2 |
|  | 0.25 | 1.9 | 2.6 | 19.1 |

TABLE 10-continued

|  | Activated carbon addition (g) | Example 3 | Comp. Ex. 5 | Comp. Ex. 6 |
|---|---|---|---|---|
| Trypsin adsorption by weight (mg/g) | 0.25 | 3.4 | 3.6 | 18.6 |
| | 0.125 | 4.8 | 6.0 | 36.5 |
| Arginine adsorption by volume (mg/mL) | 0.5 | 5.0 | 3.9 | 2.7 |
| | 0.25 | 7.8 | 5.8 | 3.9 |
| Putrescine adsorption by volume (mg/mL) | 0.5 | 2.8 | 1.2 | 0.6 |
| | 0.25 | 3.7 | 1.5 | 0.7 |
| Pullulan adsorption by volume (mg/mL) | 0.5 | 0.8 | 1.1 | 3.4 |
| | 0.25 | 1.1 | 1.3 | 7.0 |
| Trypsin adsorption by volume (mg/mL) | 0.25 | 2.0 | 1.8 | 6.8 |
| | 0.125 | 2.9 | 3.0 | 13.4 |

As clearly seen in Tables 9 and 10, the medical adsorbents of the present invention are capable of selective adsorption of ionic organic compounds.

For Example 3, Example 6, Example 10 and Comparative Example 5, 0.5 g of the activated carbon was added to 50 ml of water, the mixture was vigorously stirred for 3 hours, the mean particle size of the activated carbon after stirring was determined, and the powdering was measured as the proportion of particles of no larger than 103 μm in the particle size distribution, as described above. The results of measuring the powdering and the mean particle sizes before and after the powdering test are shown in Table 11.

TABLE 11

|  | Example 3 | Example 6 | Example 10 | Comp. Ex. 5 |
|---|---|---|---|---|
| Mean particle size before powdering (μm) | 117 | 305 | 110 | 353 |
| Mean particle size after powdering (μm) | 118 | 318 | 109 | 135 |
| Powdering (%) | 0.6 | 0.0 | 1.8 | 36.0 |

As shown in Table 11, the activated carbons of the examples had very low powdering values compared to Comparative Example 5. Also, the mean particle sizes after the powdering test were approximately equal to the values before the powdering test. Thus, the medical adsorbents of the invention were more resistant to powdering than the conventional medicinal activated carbon, and hence are assumed to be less susceptible to enteric powdering as well.

In light of the examples described above, the medical adsorbents of the present invention have adequately developed activated carbon pores and are therefore expected to exhibit satisfactory adsorption performance at lower doses than conventional medicinal activated carbon.

While the invention has been described with reference to a specific embodiment chosen for purpose of illustration, it should be apparent that numerous modifications could be made thereto by those skilled in the art without departing from the basic concept and scope of the invention.

What is claimed is:

1. A medical adsorbent comprising spherical activated carbon which is activated carbon obtained by carbonizing and activating a spherical phenol resin and which has (a) an area to weight ratio of 800-2000 m$^2$/g, (b) a pore volume of 0.2-1.0 mL/g, (c) a packing density of 0.5-0.75 g/mL, (d) a mean pore diameter of 1.7-2.0 nm, (e) a maximum particle size of no greater than 425 μm and a mean particle size of no greater than 350 μm, and (f) an overall pore volume of no greater than 0.04 mL/g of pores with pore diameters of 20-1000 nm, wherein the overall pore volume of pores with a mean pore diameter of no greater than 1.0 nm constitutes at least 55% of the total pore volume.

2. A medical adsorbent according to claim 1, wherein said spherical activated carbon has a surface oxide content of at least 0.35 meq/g.

3. A medical adsorbent according to claim 1, wherein the difference between the proportions of particles of no larger than 103 μm before and after powdering of said spherical activated carbon is no greater than 5%.

4. A process for production of a medical absorbent according to any one of claims 1, 2, and 3, which process comprises:
 a step of carbonizing a spherical phenol resin in a nitrogen atmosphere at a temperature of 400-1000° C.,
 a step of activating the carbonized spherical phenol resin at a temperature of 800-1000° C.,
 a step of washing the activated spherical phenol resin with dilute hydrochloric acid,
 a step of heat treatment at a temperature of 150-1000° C. in a mixed gas comprising oxygen and nitrogen after washing the activated spherical phenol resin with dilute hydrochloric acid, and
 a step of sorting the spherical phenol resin after said heat treatment.

5. The process for production of a medical adsorbent according to claim 4, wherein said spherical phenol resin is obtained using a phenol as the starting material.

6. The process for production of a medical adsorbent according to claim 4, wherein said spherical phenol resin is obtained using phenols including phenol and at least one methyl group bonded to a phenol nucleus as the starting materials.

* * * * *